US00PP23743P3

(12) United States Plant Patent
Roose et al.

(10) Patent No.: US PP23,743 P3
(45) Date of Patent: Jul. 16, 2013

(54) MANDARIN TREE NAMED 'KINNOWLS'

(50) Latin Name: *Citrus reticulata*
Varietal Denomination: KinnowLS

(75) Inventors: Mikeal L. Roose, Riverside, CA (US); Timothy E. Williams, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/317,428

(22) Filed: Oct. 18, 2011

(65) Prior Publication Data

US 2013/0097754 P1 Apr. 18, 2013

(51) Int. Cl.
*A01H 5/00* (2006.01)

(52) U.S. Cl.
USPC ..... Plt./201

(58) Field of Classification Search
USPC ..... Plt./201
See application file for complete search history.

(56) References Cited

PUBLICATIONS

Roose. Breeding of New Citrus Scion Varieties, California Citrus Nursery Board, Jan. 2010, 3 pp. retrieved on Jul. 26, 2012. Retrieved from the Internet at <http://www.ccnb.info/reports/2009_Roose-Scion_Breeding_Report.pdf>.*
Altaf et al. American-Eurasian J. Agric. & Environ. Sci., "Review of the Seedless Kinnow Project", 3(5); 785-788, 2008.*
Bermejo et al., Influence of Gamma Irradiation on Seedless Citrus Production: Pollen Germination and Fruit Quality, Food and Nutrition Sciences vol. 2, May 2011, 169-180.*
UCR Newsroom: UC Riverside releases new citrus variety: 'KinnowLS'. [online]. UC Riverside, Apr. 11, 2011 [retrieved on Jan. 2, 2013]. Retrieved from the Internet: <URL: http://newsroom.ucr.edu/2602>.
Roose and Williams, "'KinnowLS' Mandarin", KinnowLS—briefdescription (Jan. 2011), Dept. of Botany and Plant Sciences, University of California Riverside.

* cited by examiner

*Primary Examiner* — June Hwu
*Assistant Examiner* — Louanne Krawczewicz Myers
(74) *Attorney, Agent, or Firm* — Kilpatrick Townsend & Stockton LLP

(57) ABSTRACT

'KinnowLS' is a mid- to late-season maturing (depending on climate) diploid mandarin that combines large-sized fruit of excellent quality and production with low seed content even in mixed plantings. It may be successful in the mid-to-late season marketing window that currently has few low-seeded, high quality cultivars.

8 Drawing Sheets

Latin name of the genus and species: The mandarin cultivar of this invention is botanically identified as *Citrus reticulata.*

Variety denomination: The variety denomination is 'KinnowLS'.

BACKGROUND OF THE INVENTION

'KinnowLS' is a mandarin selection developed at Riverside, Calif. and derived from an irradiated bud of the diploid mandarin cultivar 'Kinnow' (unpatented), a mid-to-late season maturing variety. 'Kinnow' is a hybrid of two *Citrus* cultivars, 'King' (unpatented, *Citrus reticulata* 'Blanco') and 'Willowleaf' (unpatented, *Citrus reticulata* 'Blanco'), which was first developed by H. B. Frost in Riverside, Calif. After evaluation, the 'Kinnow' was released as a new variety for commercial cultivation in 1935.

Irradiation of budwood from registered 'Kinnow' trees in Exeter, Calif., was accomplished in June of 1997 in Riverside, Calif. Specifically, irradiation of 150 buds of 'Kinnow' mandarin was accomplished using 40 Gray units of gamma irradiation from a Cobalt-60 irradiation source. Buds from this irradiation were propagated onto Carrizo rootstocks in a greenhouse in Exeter, Calif. where they were grown to field-plantable-sized trees. Out of these irradiations, a total of 73 trees were obtained. This low yield of trees is typical because the radiation kills many of the buds. These trees were then planted in May 1998 in Exeter, Calif. Fruit production and evaluation began in 2001. One selection from this irradiated population (propagated on Carrizo rootstock) distinguished itself from the others in having tree growth typical of 'Kinnow' mandarin, very low seed counts in comparison to the original 'Kinnow' cultivar, and excellent fruit quality and normal fruit production characteristic of the 'Kinnow' parent. After two seasons of fruiting, this selection was given the name 'Kinnow IR5' and selected for further trials. In January 2003, buds of this selection were taken and propagated onto Carrizo and C35 citrange rootstock for field trials. In June of 2004, 72 trees, produced in Exeter, Calif., were planted at six sites (twelve trees at each site): Arvin, Irvine, Lindcove, Thermal, Riverside, and Woodlake, Calif. All trials were propagated equally on Carrizo and C35 citrange rootstocks. All trials were in mixed-plantings with other cultivars, including seedy cultivars with high pollen viability. Fruit production of these propagated trees commenced in 2006 (a few trees at each site) and 2007 (all trees at all sites). In October 2008, budwood from the selected tree was sent to Exeter, Calif. for evaluation of disease status and, as needed, elimination of viruses and other pathogens. Six trees were then established as disease-free 'mother' trees in a greenhouse in Exeter, Calif. The properties of 'KinnowLS' were found to be true to type and transmissible by asexual reproduction in comparing these plantings with the original 'KinnowLS' selection.

BRIEF SUMMARY OF THE INVENTION

'KinnowLS' is a mid-season maturing diploid mandarin that combines large-sized fruit of excellent quality and production with low seed content even in mixed plantings. It may be successful in the mid-to-late season marketing window that currently has few low-seeded, high quality cultivars.

DETAILED DESCRIPTION OF THE INVENTION

Figure 1:
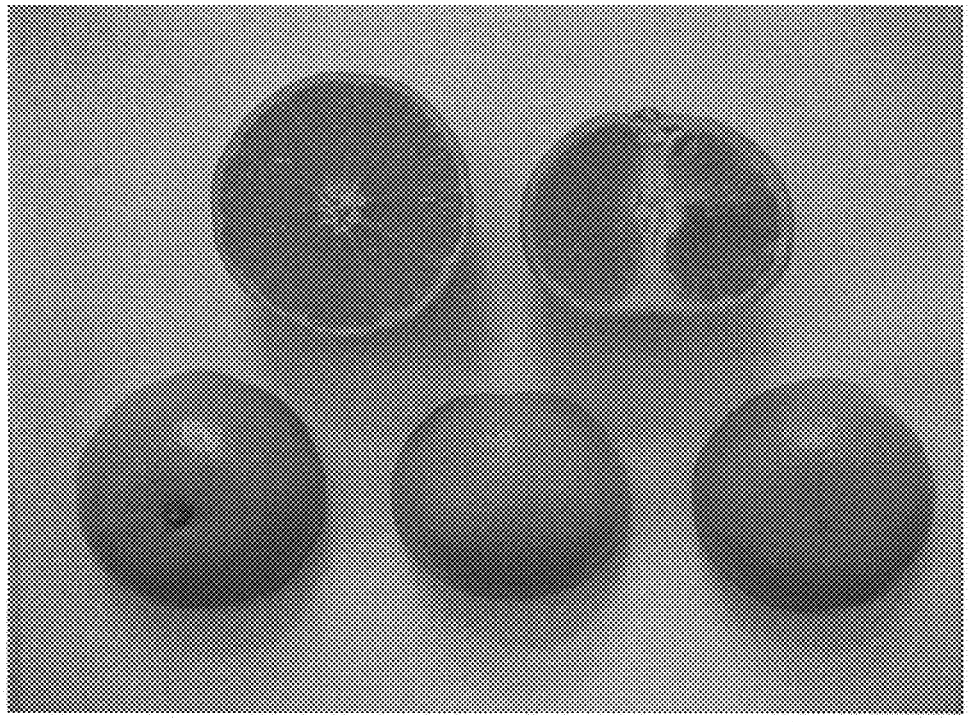
FIG. 1 shows fruit of 'KinnowLS' taken at Riverside in February.
Figure 2:
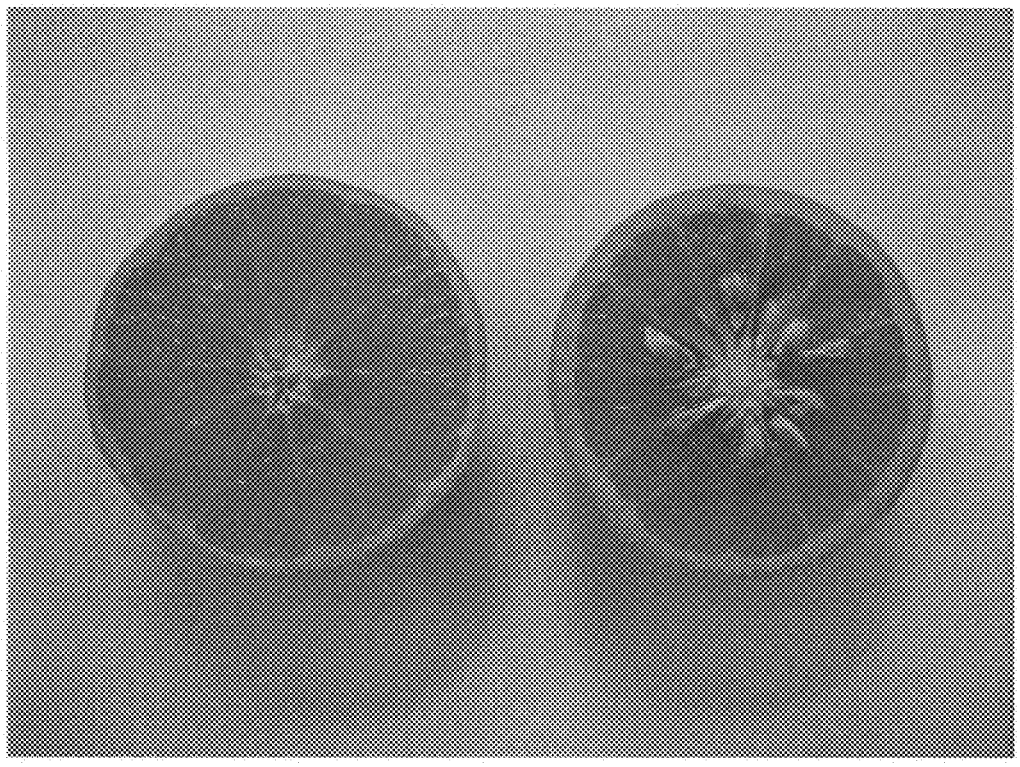
FIG. 2 shows a side-by-side comparison of (left) 'KinnowLS' and (right) 'Kinnow'.

'KinnowLS' is a mandarin selection developed at Riverside and Exeter, Calif. by mutation breeding of the mandarin cultivar 'Kinnow', for which harvest is typically begun from mid-January to mid-February, depending on location. Evaluation of 'KinnowLS' began on the original tree at Exeter, Calif. in 2001 and has continued annually until the present. 'KinnowLS' has been asexually reproduced by grafting (budding), using the standard T-bud method generally used to propagate *Citrus* in California. Asexual propagation of the selected tree was first accomplished in January 2003 at Exeter, Calif. to produce 72 trial trees on Carrizo and C35 rootstocks.

'KinnowLS' distinguishes itself by being low seeded (2-3 seeds/fruit) in all situations of cross-pollination, while 'Kinnow' has 15-30 seeds per fruit in cross-pollinated situations. At Riverside, Calif. 'KinnowLS' matures in winter (mid-January) and holds its fruit quality characteristics through April. Fruit size is large for mandarins, classed as Jumbo by State of California standards and size 21 for industry packing standards. Fruit are oblate in shape with an orange rind color and a very smooth rind texture. Flesh is deep orange in color and finely-textured. Fruit are easy to peel and juicy, with a rich, sweet and distinctive flavor when mature. Tree growth habit is vertical and vigorous, producing a large and rather dense upright crown with excellent production commencing in the third year after planting. 'KinnowLS' is well adapted to growing in all California climate zones normally associated with *Citrus*, including desert regions, because the fruit, which matures during January through April at most locations, does well in hot climates where it matures in December. Alternate bearing can be a problem in trees that are not culturally managed to reduce this tendency.

'KinnowLS' mandarin can be grown according to accepted cultural practices for larger, more vigorous mandarin varieties, including planting densities of 180-250 trees per acre, normal fertilization and pest control practices, and the use of standard rootstocks for mandarins. Other rootstocks adapted to more marginal growing conditions of salinity, high pH or very heavy soils, including the lemon types *C. macrophylla*, Volkameriana, and rough lemon, may be useful in those conditions but overall fruit quality would likely be affected negatively. Sour orange or mandarin type rootstocks such as Cleopatra might be more suitable in these marginal conditions since fruit quality would not be affected to the extent the lemon-type rootstocks impart.

'KinnowLS' is a very vigorously growing tree and therefore pruning will likely be necessary to control this vigor. Such pruning should include topping the trees to control vertical growth and selective interior pruning to enhance production and health of the tree. These pruning procedures can be applied after the second year of full fruit production and regularly thereafter.

The Royal Horticulture Society (R.H.S.) color numbering system is used herein for the color description of the rind, seed, bark, leaf, flower, flesh color and other interest of the 'KinnowLS' mandarin cultivar.

Comparison With Existing Mandarins

A comparison of 'KinnowLS' with other low-seeded late-season mandarins is provided in Table 1 below. 'KinnowLS' is distinctive in having a very wide climatic growing area (including very hot desert areas), excellent production (though some tendency to alternate bear), and fruit quality characteristics (large size, shape, very smooth rind texture, and very rich, sweet flavor) that may be preferred in some markets.

TABLE 1

Comparison of 'KinnowLS' with other late season, low-seeded mandarins. Data for Riverside, California.

| Trait | 'KinnowLS' | 'TDE2' (U.S. Plant Pat. No. 15,461) | 'TDE3' (U.S. Plant Pat. No. 15,703) |
|---|---|---|---|
| Maturity | Mid-February | February | January-February |
| Seeds per fruit | 2.45 | 0.02 | 0.29 |
| RHS rind color | Orange 25A | Orange-Red N30D | Orange-Red N30C |
| Rind texture | very smooth | slight pit | papillate |
| Fruit weight (g) | 145 | 185 | 134 |
| Fruit height/width | 0.81 | 0.78 | 0.85 |
| Alternate bearing | medium-high | medium | medium-high |

| Trait | 'TDE4' (U.S. Plant Pat. No. 16,289) | 'Gold Nugget' (unpatented) | 'Tango' (U.S. Plant Pat. No. 17,863) |
|---|---|---|---|
| Maturity | February | February-March | February |
| Seeds per fruit | 0.32 | <0.1 | 0.22 |
| RHS rind color | Orange-Red N30C | Orange 25A | Orange N25A |
| Rind texture | smooth | bumpy | smooth |
| Fruit weight (g) | 175 | 108 | 90 |
| Fruit height/width | 0.78 | 0.88 | 0.81 |
| Alternate bearing | medium-high | high | medium |

Trees, Foliage, and Flowers

Figure 3:
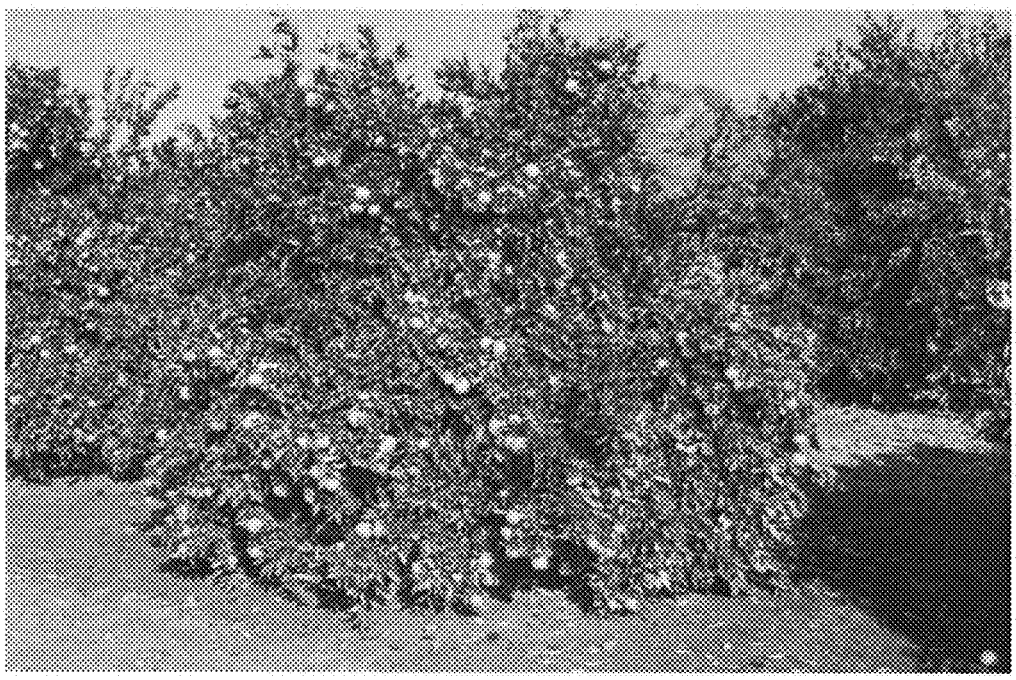
FIG. 3 shows the eleven-year old mother tree on Carrizo citrange rootstock.

Tree size and growth characteristics of 'KinnowLS' have been consistent with those of 'Kinnow' throughout the evaluations. Growth of both the 'Kinnow' and 'KinnowLS' varieties have been quite vigorous throughout the evaluation period, producing large, vertically growing trees with dense crowns. The eleven-year-old 'KinnowLS' mother tree at Lindcove, Calif. on Carrizo citrange rootstock, shown in FIG. 3, is 3.1 m high and 3.0 m wide with an upright, though beginning to spread, crown exhibiting a dense growth habit and yielding a canopy volume of 14.6 $m^3$. In comparison, an eleven-year-old 'Kinnow' control tree has averaged 3.1 m tall and 2.9 m wide, yielding a canopy volume of 13.7 $m^3$ on Carrizo citrange rootstock. These trees are smaller than normal because they were in a very high density planting until surrounding trees were removed at 7 years-of-age. In the younger, multi-location trials with more typical tree spacing, five-year-old 'KinnowLS' trees on Carrizo rootstock have averaged 3.1 m in height and 2.9 m in diameter with canopy volumes of 13.7 $m^3$. Trees on C35 rootstock averaged 3.2 m in height and 3.0 m in diameter with canopy volumes of 15.1 $m^3$.

Figure 5:
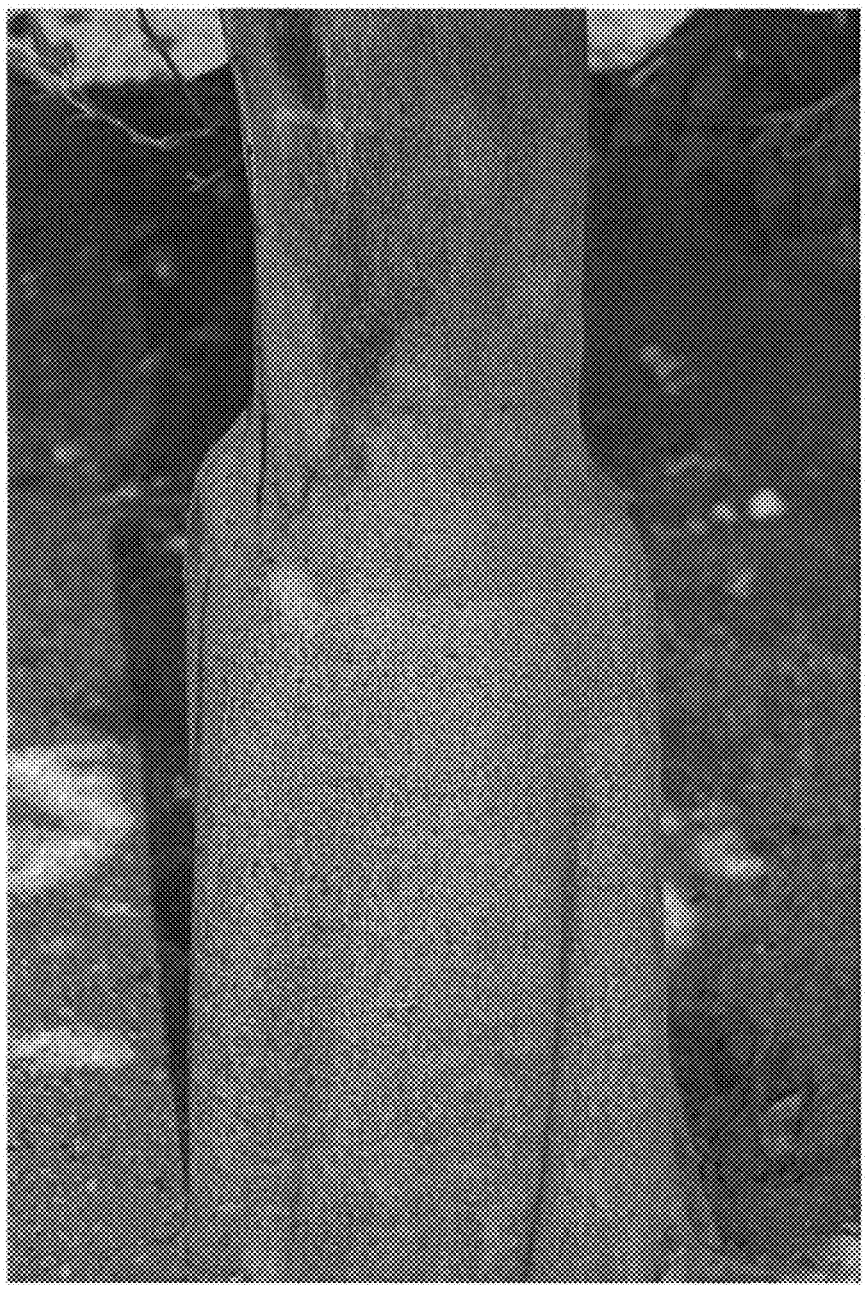
FIG. 5 shows the bud union of 'KinnowLS' on 'Carrizo' citrange rootstock, eleven-years old.

Bud unions are slightly benched, as shown in FIG. 5, resulting in a scion circumference for the eleven-year-old 'KinnowLS' mother tree on Carrizo rootstock of 44.5 cm with the rootstock circumference 56.5 cm measured 38 and 18 cm above the soil level, respectively. Scion circumference for five-year-old 'KinnowLS' trees on Carrizo rootstock averaged 40.0 cm with the rootstock circumference averaging 50.5 cm when measured about 25 and 15 cm above the soil level, respectively. Scion circumference for five-year-old 'KinnowLS' trees on C35 rootstock averaged 41.0 cm with the rootstock circumference averaging 51.5 cm when measured about 25 and 15 cm above the soil level, respectively.

Figure 7:
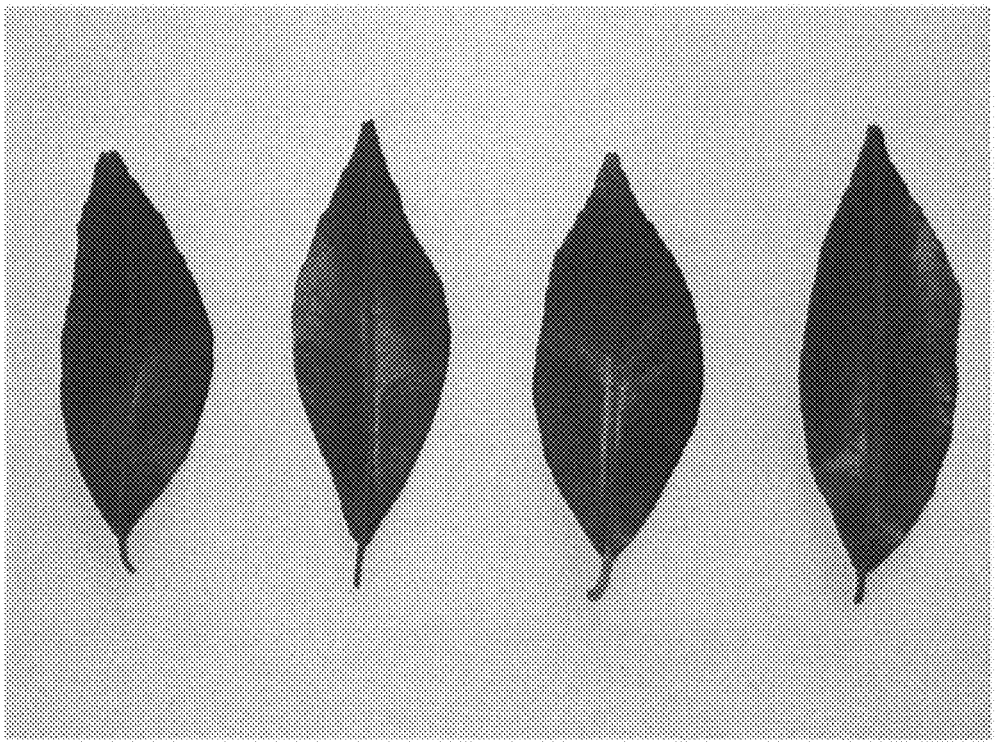
FIG. 7 shows leaves of 'KinnowLS'.

Leaves of 'KinnowLS', as shown in FIG. 7, are moderately large for a mandarin (80.8 mm in length×25.5 mm in width), lanceolate in shape and concave in cross-section and are dark-green in color (adaxial — RHS Green 137A, abaxial — RHS Yellow-Green 146B). The leaves have an acute apex with occasional weak emargination and an acute base. Petioles are medium in length (10.1 mm) and normally lack wings. The selection further lacks thorns.

Figure 8:
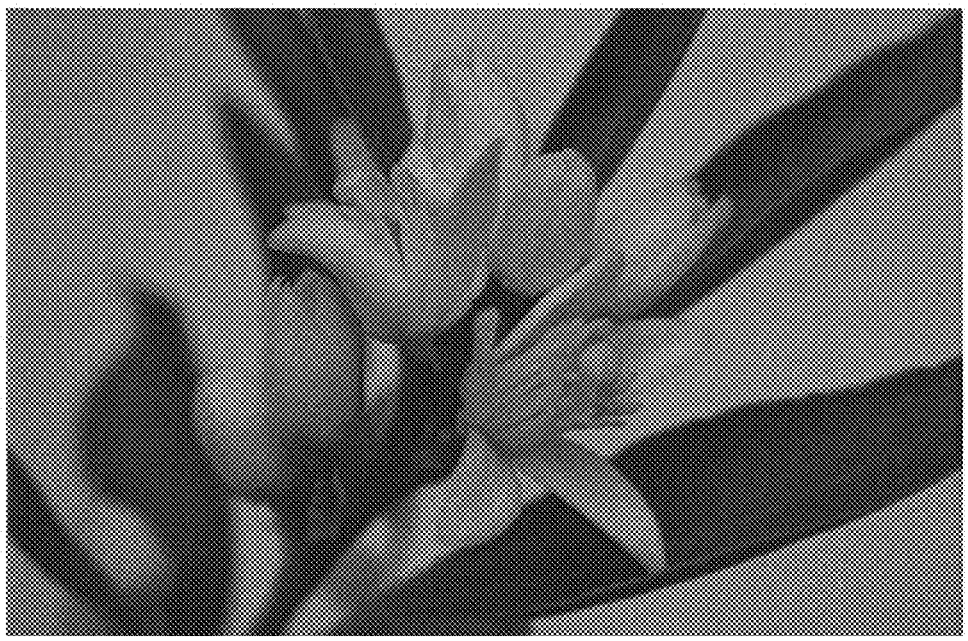
FIG. 8 shows open and closed flowers of 'KinnowLS'.

As shown in FIG. 8, flowers of 'KinnowLS' are hermaphroditic, borne in clusters, medium in length, with greenish-white (RHS Green White 157D, adaxial and abaxial) petals averaging 13.1 mm in length and 6.2 mm in width, and with about 18 anthers which are yellowish in color (Yellow 13B). The five sepals are rudimentary, yellow-green (RHS Yellow Green 1D) in color and partly fused into a calyx. The free portion of the sepals averages 1.53 mm in length and 1.97 mm in width. The fused portion is about 1.0 mm in length. Pollen is yellowish in color (RHS Yellow 12B).

TABLE 2

Tree, leaf, flower and seed characteristics (for eleven-year-old tree) of 'KinnowLS' mandarin on Carrizo.

| | |
|---|---|
| 1. Tree height | 3.1 m |
| 2. Crown diameter | 3.0 m |
| 3. Crown shape/density | Upright, spreading with age and dense |
| 4. Scion circumference | 44.5 cm |
| 5. Height scion measured above soil surface | 38 cm |
| 6. Rootstock circumference | 56.5 cm |
| 7. Height Carrizo rootstock measured above soil surface | 18 cm |
| 8. Scion circumference[z] | 40.0 cm |
| 9. Rootstock circumference[z] | 50.5 cm |
| 10. Scion circumference[y] | 41.0 cm |
| 11. Rootstock circumference[y] | 51.5 cm |
| 12. Bud-union characteristics (on citrange rootstock) | Slightly benched (scion diameter smaller than rootstock) |
| 13. Rootstock-scion compatibility | No evidence of incompatibility in trees Carrizo citrange at 11 years old (mother tree) or on C35 citrange at 7 years old (trial trees) |
| 14. Tree vigor | Vigorous |
| 15. Bark color | RHS Grey-Brown N199A |
| 16. Leaf shape | Lanceolate |

TABLE 2-continued

Tree, leaf, flower and seed characteristics (for eleven-year-old tree) of 'KinnowLS' mandarin on Carrizo.

| | |
|---|---|
| 17. Leaf cross-section | Concave |
| 18. Leaf blade length | 80.8 mm |
| 19. Leaf blade width | 25.5 mm |
| 20. Leaf apex | Acute with weak emargination |
| 21. Leaf base | Acute |
| 22. Leaf margins | Very slightly crenate |
| 23. Leaf abaxial color | RHS Yellow-Green 146B |
| 24. Leaf adaxial color | RHS Green 137A |
| 25. Petiole length | 10.1 mm ± 0.7 |
| 26. Petiole width | 1.5 mm |
| 27. Petiole wings | Absent |
| 28. Petiole color | RHS Green 137A |
| 29. Thorniness | Not present |
| 30. Inflorescence type | Clustered |
| 31. Flowering habit | Flowers once per year |
| 32. Flower structure | Complete |
| 33. Bud length (one day before opening) | 12.2 mm |
| 34. Bud width (one day before opening) | 7.5 mm |
| 35. Bud shape (one day before opening) | oblong |
| 36. Petal number | 5 |
| 37. Sepal number | 5 |
| 38. Petal length | 13.1 mm |
| 39. Petal width | 6.2 mm |
| 40. Petal apex | acute |
| 41. Petal base | truncate |
| 42. Petal color (adaxial) | RHS Green-White 157D |
| 43. Petal color (abaxial) | RHS Green-White 157D |
| 44. Petal shape | elliptic |
| 45. Petal margin | smooth |
| 46. Sepal number | 5 |
| 47. Sepal color | RHS Yellow-Green 1D |
| 48. Sepal shape | partly fused, tips attenuate |
| 49. Sepal length (free portion) | 1.53 mm |
| 50. Sepal width | 1.97 mm |
| 51. Number of anthers | 18 (range 17-20) |
| 52. Anther color | RHS Yellow 13B |
| 53. Pollen color | RHS Yellow 12B |
| 54. Pollen viability | Moderately low (15-25%) |

[z,y]Bud union measurements are averages for 5-year-old trial trees on Carrizo[z] or C35[y] measured about 10 cm above (for scion) and 10 cm below (for rootstock) budunion, generally about 15 and 25 cm above soil.

Pollen viability for 'KinnowLS' is moderately low (15-25% germination) in comparison to 'Kinnow' (~70% germination), and pollen production in comparison to normal 'Kinnow' is significantly reduced. These pollen characteristics suggest that 'KinnowLS' will not cause appreciable seediness in adjacent varieties. Crosses of 'KinnowLS' pollen onto Clemenules and W. Murcott gave low fruit set (6 and 9% respectively) and fruit set from these pollinations had few seeds (average 1.8 and 2.2 seeds/fruit respectively).

Fruiting, Fruit and Production Characteristics

As shown in FIG. 1, fruit of 'KinnowLS' are oblate in shape with no neck. The fruit has a rounded basal end which is flattened at the stem attachment point with a truncate (slightly depressed) distal end. The fruit is large-sized for a mandarin (classed as Jumbo by State of California standards and size 21 for industry packing standards) averaging 2.7 in (68.0 mm) in diameter and 2.2 in (55.2 mm) in height. Fruit average 0.32 lb (145 g) in weight. It has a very smooth, orange color rind and slightly conspicuous, slightly depressed oil glands. The rind is slightly adherent at maturity and relatively thin, averaging 0.1 in (2.5 mm) in thickness. Fruit peel easily. The fruit interior has a moderately fine flesh texture with 10-11 segments and is quite juicy, averaging 49% juice. Fruit from trees on Carrizo and C35 citrange rootstocks average 12.2-13.9% soluble solids and 1.26-2.09% acid in mid-January at four trial locations in California increasing in soluble solids to 13.5-15.8% with acid decreasing to 0.97-1.98% in mid-February. By mid-March juice averaged 13.3-17.0% soluble solids and 0.80-1.87% acid. Fruit generally continue to increase in soluble solids and decrease in acidity well into April and May at all trial sites. See Tables 4a-4b below for mean and standard deviation of soluble solids, acid and solids/acid ratio for 'KinnowLS' on various rootstocks from 2007 to 2009. The earliest recommended harvest date occurs when fruit reach average soluble solids content of at least 12% and an average acid content of less than 1.2%. This may occur as early as late November in hot desert regions (Coachella Valley of Calif.), but can be as late as early April in cool locations (Irvine, Calif.) or years (2008-9).

Based on evaluation of an average of 1500 fruit per location, fruit average 2.45 seeds per fruit in the presence of heavy cross-pollination at all locations from 2007 to 2009. Rarely, individual fruit may have 4-7 seeds. In the 2010-11 season one tree was identified with a branch on which most fruit had high seed content (more than 10 seeds/fruit). However, for 5200 fruit sampled from trail trees during 2009-10 and 2010-2011, the percentage of seedy fruit was about 0.06%. Seeds are polyembryonic. See Table 5 below for average number of seeds per fruit for 'KinnowLS' and 'Kinnow' (control trees) from 2007 to 2009. Seeds are polyembryonic, with a wrinkled surface and greyed yellow seed coat (RHS 161C). Seeds average about 140 mg in weight, with about 10% of seeds much smaller and apparently lacking developed embryos.

TABLE 3

Fruit characteristics of 'KinnowLS' mandarin at maturity

| | |
|---|---|
| 1. Fruit shape | Oblate |
| 2. Fruit diameter | 68.0 mm ± 2.8 |
| 3. Fruit height | 55.2 mm ± 2.1 |
| 4. Aspect ratio (height/diameter) | 0.81 |
| 5. Fruit: shape of basal end | Rounded (flattened at stem) |
| 6. Fruit: shape of distal end | Truncate (slightly depressed) |
| 7. Fruit: distal end areola | Present but faint |
| 8. Fruit: distal end areola diameter | 18.8 mm |
| 9. Fruit neck | Not present |
| 10. Style | Not persistent |
| 11. Rind texture | Very smooth |
| 12. Oil glands | Slightly conspicuous, slightly depressed |
| 13. Rind Color | RHS Orange 25A |
| 14. Rind thickness | 2.5 mm |
| 15. Albedo thickness | 1.5 mm |
| 16. Albedo color | RHS Orange-White 159A |
| 17. Rind adherence | Medium-Low |
| 18. Rind separation | Slight |
| 19. Flesh (pulp) color | RHS Orange N25B |
| 20. Flesh (pulp) texture | Moderately fine |
| 21. Number of segments | 10-11 |
| 22. Axis: structure | Semi-solid |
| 23. Axis: size | Medium |
| 24. Navel presence | Not present |
| 25. # Seeds/fruit (mean) | 2.45 (cross-pollinated conditions) |
| 26. Seed embryony | Polyembryonic |
| 27. Seed coat color | Greyed-Yellow 161C |
| 28. Seed cotyledon color | Greyed-Yellow 160C |
| 29. Seed inner coat color | Greyed-Brown 199D |
| 30. Seed weight | 140 mg |
| 31. Seed length | 12.2 mm |
| 32. Seed width | 6.0 mm |
| 33. Seed thickness | 4.2 mm |
| 34. Fruit weight | 145 g |
| 35. % Juice | 49.1% |
| 36. % Soluble solids (at peak maturity) | 14.7% |
| 37. % Acid (at peak maturity) | 1.18% |
| 38. Season of maturity | Late (January-May in Northern Hemisphere) |

TABLE 3-continued

Fruit characteristics of 'KinnowLS' mandarin at maturity

| | |
|---|---|
| 39. Fruit holding ability on tree past maturity | Excellent (6-8 weeks) |
| 40. Fruit quality after storage (5.6° C., 30 days) | Very Good |

TABLE 4a

Mean of soluble solids, acid and solids/acid ratio for 'KinnowLS' on Carrizo and C35 citrange rootstock at four trial sites for the 2007/8 crop year.

| Site | Dates Sampled | # Trees | Tree Age In 2008 (yrs) | Soluble Solids % Carrrizo | Soluble Solids % C35 |
|---|---|---|---|---|---|
| Riverside | Jan. 15, 2008 | 6 | 4 | 13.2 | 13.1 |
| Riverside | Feb. 14, 2008 | 5 | 4 | 14.6 | 14.8 |
| Riverside | Mar. 12, 2008 | 3 | 4 | 16.5 | 16.6 |
| Lindcove | Jan. 14, 2008 | 6 | 4 | 13.0 | 12.8 |
| Lindcove | Feb. 12, 2008 | 6 | 4 | 14.5 | 14.3 |
| Lindcove | Mar. 13, 2008 | 3 | 4 | 16.4 | 16.9 |
| Irvine | Jan. 16, 2008 | 6 | 4 | 12.2 | 12.3 |
| Irvine | Feb. 15, 2008 | 6 | 4 | 13.9 | 13.5 |
| Irvine | Mar. 11, 2008 | 4 | 4 | 15.1 | 14.6 |
| Arvin | Jan. 15, 2008 | 6 | 4 | 13.6 | 13.1 |
| Arvin | Feb. 13, 2008 | 6 | 4 | 14.8 | 14.4 |
| Arvin | Mar. 14, 2008 | 4 | 4 | 15.7 | 15.6 |

| Site | Dates Sampled | % Acid Carrizo | % Acid C35 | S/A Ratio Carrizo | S/A Ratio C35 |
|---|---|---|---|---|---|
| Riverside | Jan. 15, 2008 | 1.60 | 1.66 | 8.3 | 7.9 |
| Riverside | Feb. 14, 2008 | 1.41 | 1.45 | 10.4 | 10.2 |
| Riverside | Mar. 12, 2008 | 1.19 | 1.25 | 13.7 | 13.3 |
| Lindcove | Jan. 14, 2008 | 1.29 | 1.36 | 10.1 | 9.4 |
| Lindcove | Feb. 12, 2008 | 1.20 | 1.26 | 12.1 | 11.3 |
| Lindcove | Mar. 13, 2008 | 0.91 | 0.90 | 18.0 | 18.8 |
| Irvine | Jan. 16, 2008 | 1.88 | 1.69 | 6.5 | 7.3 |
| Irvine | Feb. 15, 2008 | 1.50 | 1.56 | 9.3 | 8.7 |
| Irvine | Mar. 11, 2008 | 1.21 | 1.18 | 12.5 | 12.4 |
| Arvin | Jan. 15, 2008 | 1.20 | 1.23 | 11.3 | 10.7 |
| Arvin | Feb. 13, 2008 | 1.03 | 1.07 | 14.4 | 13.5 |
| Arvin | Mar. 14, 2008 | 0.88 | 0.90 | 17.8 | 17.3 |

TABLE 4b

Mean of soluble solids, acid and solids/acid ratio for 'KinnowLS' on Carrizo and C35 citrange rootstock at four trial sites for the 2008/9 crop year.

| Site | Dates Sampled | # Trees | Tree Age In 2009 (yrs) | Soluble Solids % Carrrizo | Soluble Solids % C35 |
|---|---|---|---|---|---|
| Riverside | Jan. 15, 2009 | 6 | 5 | 15.6 | 16.5 |
| Riverside | Feb. 4, 2009 | 5 | 5 | 15.8 | 15.8 |
| Riverside | Feb. 25, 2009 | 5 | 5 | 16.2 | 16.5 |
| Riverside | Mar. 16, 2009 | 3 | 5 | 16.9 | 17.0 |
| Lindcove | Jan. 13, 2009 | 6 | 5 | 13.4 | 13.9 |
| Lindcove | Feb. 2, 2009 | 6 | 5 | 13.4 | 14.5 |
| Lindcove | Mar. 14, 2009 | 3 | 5 | 14.0 | 14.4 |
| Lindcove | Apr. 1, 2009 | 3 | 5 | 15.6 | 15.5 |
| Irvine | Jan. 7, 2009 | 6 | 5 | 13.7 | 13.9 |
| Irvine | Jan. 26, 2009 | 6 | 5 | 13.5 | 14.3 |
| Irvine | Feb. 24, 2009 | 6 | 5 | 13.4 | 14.6 |
| Irvine | Mar. 16, 2009 | 4 | 5 | 13.4 | 14.7 |
| Irvine | Mar. 30, 2009 | 4 | 5 | 13.4 | 14.9 |
| Arvin | Jan. 14, 2009 | 6 | 5 | 13.3 | 12.3 |
| Arvin | Feb. 3, 2009 | 6 | 5 | 12.6 | 12.1 |

TABLE 4b-continued

Mean of soluble solids, acid and solids/acid ratio for 'KinnowLS' on Carrizo and C35 citrange rootstock at four trial sites for the 2008/9 crop year.

| | | | | | |
|---|---|---|---|---|---|
| Arvin | Mar. 14, 2009 | 4 | 5 | 13.3 | 13.4 |
| Arvin | Apr. 1, 2009 | 4 | 5 | 15.3 | 14.1 |

| Site | Dates Sampled | % Acid Carrizo | % Acid C35 | S/A Ratio Carrizo | S/A Ratio C35 |
|---|---|---|---|---|---|
| Riverside | Jan. 15, 2009 | 2.09 | 2.21 | 7.5 | 7.5 |
| Riverside | Feb. 4, 2009 | 1.78 | 1.98 | 8.9 | 8.0 |
| Riverside | Feb. 25, 2009 | 1.68 | 1.99 | 9.6 | 8.3 |
| Riverside | Mar. 16, 2009 | 1.50 | 1.87 | 11.3 | 9.1 |
| Lindcove | Jan. 13, 2009 | 1.26 | 1.47 | 10.6 | 9.5 |
| Lindcove | Feb. 2, 2009 | 1.18 | 1.17 | 11.4 | 12.4 |
| Lindcove | Mar. 14, 2009 | 0.80 | 0.97 | 17.5 | 14.8 |
| Lindcove | Apr. 1, 2009 | 0.70 | 0.89 | 22.3 | 17.4 |
| Irvine | Jan. 7, 2009 | 1.88 | 2.11 | 7.3 | 6.6 |
| Irvine | Jan. 26, 2009 | 1.79 | 2.62 | 7.5 | 5.5 |
| Irvine | Feb. 24, 2009 | 1.64 | 1.94 | 8.2 | 7.5 |
| Irvine | Mar. 16, 2009 | 1.37 | 1.77 | 9.8 | 8.3 |
| Irvine | Mar. 30, 2009 | 1.18 | 1.59 | 11.4 | 9.4 |
| Arvin | Jan. 14, 2009 | 1.17 | 1.16 | 11.4 | 10.6 |
| Arvin | Feb. 3, 2009 | 0.97 | 1.11 | 13.0 | 10.9 |
| Arvin | Mar. 14, 2009 | 0.80 | 0.87 | 16.6 | 15.4 |
| Arvin | Apr. 1, 2009 | 0.76 | 0.75 | 20.1 | 18.8 |

TABLE 5

Seed counts (average number of seeds per fruit) for 'KinnowLS' and 'Kinnow' (control trees) at four trial sites over two years, 2007/2008 and 2008/2009.

| Site | Selection | # Trees | Tree Age In 2009 (yrs) | Rootstock |
|---|---|---|---|---|
| Riverside | 'KinnowLS' | 6 | 5 | Carrizo |
| Riverside | 'KinnowLS' | 5 | 5 | C35 |
| Riverside | 'Kinnow' control | 3 | 5 | Carrizo/C35 |
| Lindcove | 'KinnowLS' | 6 | 5 | Carrizo |
| Lindcove | 'KinnowLS' | 6 | 5 | C35 |
| Lindcove | 'Kinnow' control | 3 | 5 | Carrizo/C35 |
| Lindcove | 'KinnowLS' (mother tree) | 1 | 11 | Carrizo |
| Irvine | 'KinnowLS' | 6 | 5 | Carrizo |
| Irvine | 'KinnowLS' | 6 | 5 | C35 |
| Irvine | 'Kinnow' control | 4 | 5 | Carrizo/C35 |
| Arvin | 'KinnowLS' | 6 | 5 | Carrizo |
| Arvin | 'KinnowLS' | 6 | 5 | C35 |
| Arvin | 'Kinnow' control | 4 | 5 | Carrizo/C35 |

| Site | Selection | 2007/8 Mean Seeds/Fruit (range/tree) | 2008/9 Mean Seeds/Fruit (range/tree) |
|---|---|---|---|
| Riverside | 'KinnowLS' | 2.4 (1.6-3.0) | 2.3 (2.1-3.0) |
| Riverside | 'KinnowLS' | 2.2 (1.5-2.9) | 2.4 (1.9-3.1) |
| Riverside | 'Kinnow' control | 18.9 (17.4-20.6) | 20.8 (18.8-22.1) |
| Lindcove | 'KinnowLS' | 2.8 (2.3-3.1) | 2.6 (2.2-2.9) |
| Lindcove | 'KinnowLS' | 2.4 (1.7-2.9) | 2.5 (2.0-3.0) |
| Lindcove | 'Kinnow' control | 26.2 (22.1-27.5) | 22.3 (19.7-23.7) |
| Lindcove | 'KinnowLS' (mother tree) | 2.4 | 2.1 |
| Irvine | 'KinnowLS' | 2.0 (1.7-2.8) | 1.8 (0.8-2.3) |
| Irvine | 'KinnowLS' | 1.9 (1.4-2.6) | 2.4 (1.4-2.9) |
| Irvine | 'Kinnow' control | 20.6 (17.8-22.1) | 18.6 (16.9-19.7) |
| Arvin | 'KinnowLS' | 1.6 (0.8-1.9) | 1.8 (0.9-2.2) |
| Arvin | 'KinnowLS' | 1.4 (1.0-2.0) | 1.5 (0.7-2.1) |

TABLE 5-continued

Seed counts (average number of seeds per fruit) for 'KinnowLS' and 'Kinnow' (control trees) at four trial sites over two years, 2007/2008 and 2008/2009.

| | | |
|---|---|---|
| Arvin | 'Kinnow' control | 22.1 (18.6-24.5) | 17.9 (17.3-18.4) |

| Site | Selection | % Fruit with 0-3 seeds (2008/9) |
|---|---|---|
| Riverside | 'KinnowLS' | 87.3 |
| Riverside | 'KinnowLS' | 88.8 |
| Riverside | 'Kinnow' control | 0 |
| Lindcove | 'KinnowLS' | 86.9 |
| Lindcove | 'KinnowLS' | 90.7 |
| Lindcove | 'Kinnow' control | 0 |
| Lindcove | 'KinnowLS' (mother tree) | 89.1 |
| Irvine | 'KinnowLS' | 86.5 |
| Irvine | 'KinnowLS' | 91.4 |
| Irvine | 'Kinnow' control | 0 |
| Arvin | 'KinnowLS' | 91.2 |
| Arvin | 'KinnowLS' | 87.1 |
| Arvin | 'Kinnow' control | 0 |

Figure 4:
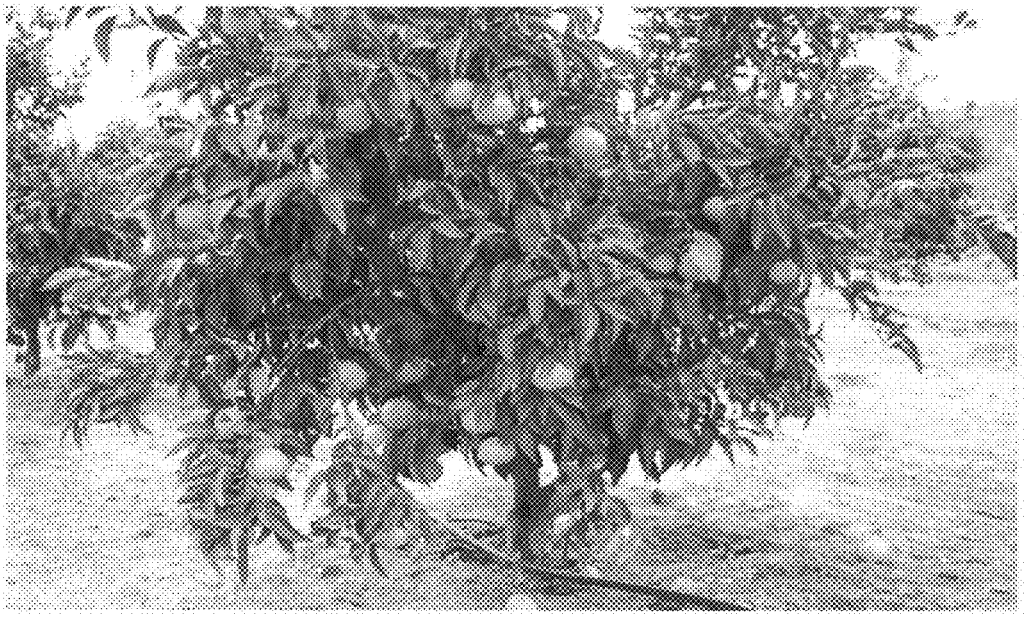
FIG. 4 shows a three-year old 'KinnowLS' tree in Exeter, Calif.
Figure 6:
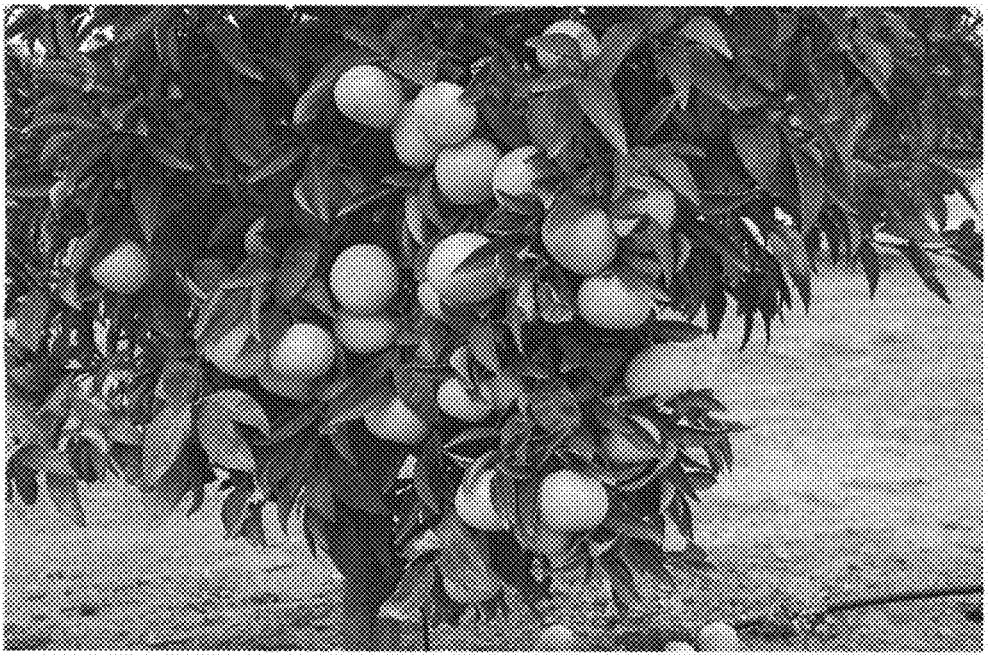
FIG. 6 shows fruit clusters on a three-year old 'KinnowLS' tree in Exeter, Calif. in the month of February.

Full fruit production of 'KinnowLS' normally begins in the third year after planting, however trees can be precocious and set some fruit in the second year after planting. FIGS. 4 and 6 illustrate fruit production on a three-year old tree. 'KinnowLS', is similar to 'Kinnow' in reaching high production levels relatively quickly. Mean yield of five year-old trees ranged from 152-211 lb (69-96 kg) on Carrizo rootstock and 165-196 lb (75-89 kg) on C35 rootstock at the four fruiting trial sites. The original 'KinnowLS' mother tree at Lindcove, Calif. produced 156 lb (71 kg) in the fifth year and in years 9, 10 and 11 yielded 191, 101, 240 lb of fruit respectively, which indicates that the variety has somewhat of a tendency to alternate bearing. In this respect, it is similar to 'Kinnow', which can exhibit severe alternate bearing if the crop is not managed to reduce overproduction in 'on' years.

TABLE 6

Crop yields for 'KinnowLS' and 'Kinnow' (control trees) at three trial sites over two years, 2007/2008 and 2008/2009

| Site | Selection | # Trees | Tree Age in 2009 (yrs) | Rootstock | 2007/8 Mean Yield (kg) |
|---|---|---|---|---|---|
| Riverside | 'KinnowLS' | 6 | 5 | Carrizo | 40 |
| Riverside | 'KinnowLS' | 5 | 5 | C35 | 32 |
| Riverside | 'Kinnow' control | 3 | 5 | Carrizo/C35 | 36 |
| Lindcove | 'KinnowLS' | 6 | 5 | Carrizo | 59 |
| Lindcove | 'KinnowLS' | 6 | 5 | C35 | 63 |
| Lindcove | 'Kinnow' control | 3 | 5 | Carrizo/C35 | 52 |
| Lindcove | 'KinnowLS' (mother tree) | 1 | 11 | Carrizo | 46 |
| Irvine | 'KinnowLS' | 6 | 5 | Carrizo | 44 |
| Irvine | 'KinnowLS' | 6 | 5 | C35 | 47 |
| Irvine | 'Kinnow' control | 4 | 5 | Carrizo/C35 | 39 |
| Arvin | 'KinnowLS' | 6 | 5 | Carrizo | 70 |
| Arvin | 'KinnowLS' | 6 | 5 | C35 | 73 |
| Arvin | 'Kinnow' control | 4 | 5 | Carrizo/C35 | 64 |

| Site | Selection | 2007/8 Yield Range (kg) | 2008/9 Mean Yield (kg) | 2008/9 Yield Range (kg) |
|---|---|---|---|---|
| Riverside | 'KinnowLS' | 28-46 | 71 | 59-83 |
| Riverside | 'KinnowLS' | 20-36 | 75 | 48-89 |
| Riverside | 'Kinnow' control | 32-39 | 62 | 51-74 |
| Lindcove | 'KinnowLS' | 49-66 | 69 | 22-90 |
| Lindcove | 'KinnowLS' | 54-71 | 78 | 55-87 |
| Lindcove | 'Kinnow' control | 45-58 | 28 | 17-31 |

TABLE 6-continued

Crop yields for 'KinnowLS' and 'Kinnow' (control trees) at three trial sites over two years, 2007/2008 and 2008/2009

| | | | | |
|---|---|---|---|---|
| Lindcove | 'KinnowLS' (mother tree) | 46 | 109 | 109 |
| Irvine | 'KinnowLS' | 35-50 | 72 | 33-91 |
| Irvine | 'KinnowLS' | 34-55 | 76 | 53-88 |
| Irvine | 'Kinnow' control | 30-44 | 58 | 31-80 |
| Arvin | 'KinnowLS' | 61-86 | 96 | 81-110 |
| Arvin | 'KinnowLS' | 60-89 | 89 | 78-112 |
| Arvin | 'Kinnow' control | 55-74 | 91 | 75-105 |

Fruit storage trials included storage of washed but not waxed fruit at 5.6° C. for up to 30 days with fruit samples taken every 15 days for analysis. Data indicates that the storage characteristics of 'KinnowLS' are very good with very little measureable loss of rind quality or color, no significant loss in juice quality or deterioration in taste, and no significant indication of fungal or other disease problems over the 30 day storage period. Overall 'KinnowLS' can be considered to be very good in storage ability for 4-6 weeks under controlled environment storage conditions.

No susceptibilities to plant or fruit diseases, or to pests, beyond those normally associated with *Citrus* species, have been observed.

What is claimed is:

1. A new and distinct mandarin tree having the characteristics substantially as described and illustrated herein.

* * * * *